United States Patent
Field et al.

(10) Patent No.: US 9,625,591 B2
(45) Date of Patent: Apr. 18, 2017

(54) RADIATION DETECTOR PROBE FOR IONISING RADIATION

(75) Inventors: Robert Shaun Field, Cleveland (GB); Geoffrey Stuart Howe, Durham (GB); Simon Lambert, Cleveland (GB)

(73) Assignee: JOHNSON MATTHEY PLC, London (GB)

( * ) Notice: Subject to any disclaimer, the term of this patent is extended or adjusted under 35 U.S.C. 154(b) by 0 days.

(21) Appl. No.: 14/238,551

(22) PCT Filed: Aug. 16, 2012

(86) PCT No.: PCT/GB2012/052008
§ 371 (c)(1),
(2), (4) Date: Feb. 12, 2014

(87) PCT Pub. No.: WO2013/024301
PCT Pub. Date: Feb. 21, 2013

(65) Prior Publication Data
US 2014/0175290 A1    Jun. 26, 2014

(30) Foreign Application Priority Data
Aug. 17, 2011    (GB) .................................. 1114151.2

(51) Int. Cl.
*G01F 23/28*    (2006.01)
*G01T 1/18*    (2006.01)
*G01T 7/00*    (2006.01)
*G01F 23/288*    (2006.01)
*G01N 9/24*    (2006.01)
(Continued)

(52) U.S. Cl.
CPC ............. *G01T 7/00* (2013.01); *G01F 23/288* (2013.01); *G01F 23/2885* (2013.01); *G01N 9/24* (2013.01); *G01T 1/18* (2013.01); *G01T 1/20* (2013.01); *G01T 3/008* (2013.01); *G01T 3/06* (2013.01)

(58) Field of Classification Search
CPC .................................................... G01F 23/2885
See application file for complete search history.

(56) References Cited

U.S. PATENT DOCUMENTS 2,830,183 A    4/1958   Wolfe
4,423,329 A *  12/1983  De Burgos Garcia .... G01T 1/18
                                                       250/374
(Continued)

FOREIGN PATENT DOCUMENTS

EP    0 101 353    2/1984
EP    0 262 524    4/1988
(Continued)

OTHER PUBLICATIONS

International Search Report dated Mar. 14, 2013, corresponding to PCT/GB2012/052008.
(Continued)

*Primary Examiner* — Casey Bryant
(74) *Attorney, Agent, or Firm* — Young & Thompson

(57) ABSTRACT

A detector probe for detecting ionizing radiation includes at least one detector (14) mounted on a support (12), and an electrically operated source of heat (18) arranged on the support in proximity to the detector so that the temperature of the detector may be changed by operation of the heat source. The detector probe may be used in the manufacture of a level gauge or density profiler.

17 Claims, 2 Drawing Sheets

Figure 1:
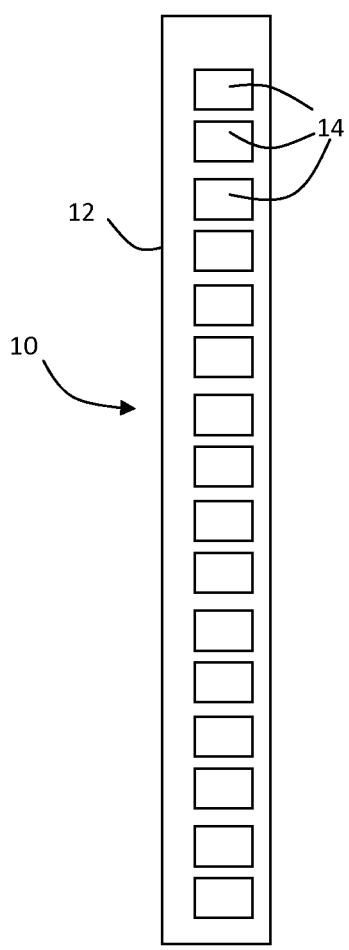

(51) Int. Cl.
    *G01T 1/20*     (2006.01)
    *G01T 3/00*     (2006.01)
    *G01T 3/06*     (2006.01)

(56) References Cited

U.S. PATENT DOCUMENTS

| | | | |
|---|---|---|---|
| 4,672,544 | A | 6/1987 | Chizallet et al. |
| 4,810,885 | A | 3/1989 | Persyk et al. |
| 5,098,641 | A * | 3/1992 | Shiraishi .............. G21C 17/038 376/153 |
| 5,103,092 | A | 4/1992 | Takahashi |
| 5,196,704 | A | 3/1993 | Miller |
| 2003/0168605 | A1 | 9/2003 | Chambaud |
| 2004/0025569 | A1 | 2/2004 | Damm |
| 2005/0086948 | A1 | 4/2005 | Milke-Rojo |
| 2007/0090059 | A1 * | 4/2007 | Plummer ................ C02F 1/008 210/743 |
| 2010/0140480 | A1 | 6/2010 | Rauer et al. |

FOREIGN PATENT DOCUMENTS

| | | |
|---|---|---|
| GB | 2326232 | 12/1998 |
| WO | 00/22387 | 4/2000 |
| WO | 01/71383 | 9/2001 |
| WO | 2010/032064 | 3/2010 |

OTHER PUBLICATIONS

British Search Report dated Nov. 26, 2012, corresponding to the Foreign Priority Application No. GB1214647.8.
European Patent Office Examination report dated Jan. 10, 2017.

\* cited by examiner

RADIATION DETECTOR PROBE FOR IONISING RADIATION

BACKGROUND OF THE INVENTION

Field of the Invention

The present invention relates to an apparatus for measuring levels of materials, especially of fluids, and optionally for calculating a density profile of a mixed fluid system.

Description of the Related Art

A density profiler has been described in WO2000/022387. The device comprises a linear array of sources of ionising radiation which emit radiation towards detectors disposed in one or more linear arrays. When the source array and detector array(s) are positioned so that they traverse the interfaces between two or more fluids in a container, the interfaces of the fluids may be identified from the differences in radiation received by each detector in the array. The device has been successfully deployed for use in storage tanks and oil separators. In some circumstances it is required to operate density profilers in cold environments or where there is a risk that the instrument will be subjected to very low temperatures at certain times. Many electronic instruments are sensitive to operation in extreme temperatures and electrical components may be prone to failure or may not be certified for operation at extremely low temperatures. It is therefore an object of the invention to provide a detector probe suitable for use in a density profiler or other nucleonic level measurement system which may be operated at low environmental temperatures.

SUMMARY OF THE INVENTION

According to the invention we provide a detector probe for detecting ionising radiation comprising:
- at least one radiation detector for detecting ionising radiation comprising alpha particles, beta particles, gamma radiation and/or neutrons, and a support and an electrically operated source of heat arranged in proximity to the detector so that the temperature of the detector may be changed by operation of the heat source.

According to a second aspect of the invention, we provide a level gauge for measuring a level of a material within a container, comprising a source of ionising radiation and a detector probe for detecting ionising radiation comprising at least one detector mounted on a support, said source and detector probe being arranged so that ionising radiation from the source passes along a straight line through a portion of the container to the detector probe; characterised in that said detector probe further comprises an electrically operated source of heat arranged in proximity to the detector so that the temperature of the detector may be changed by operation of the heat source.

According to a third aspect of the invention, we provide a density profiler for measuring a level of two or more material phases within a container, comprising a linear array of sources of ionising radiation, at least one detector probe for detecting ionising radiation comprising a linear array of radiation detectors mounted on a support, and a signal and data processing means for calculating a density profile of the material phases using signals generated by the detectors in response to radiation received from the sources; said source array and detector probe being arranged so that ionising radiation from each source passes along a straight line through a portion of the container to a detector carried on the detector probe; characterised in that said detector probe further comprises an electrically operated source of heat arranged in proximity to the detector so that the temperature of the detector may be changed by operation of the heat source.

The detector probe comprises at least one radiation detector for detecting ionising radiation comprising, or consisting of alpha particles, beta particles, gamma radiation and neutrons emitted by a radiation source. The type of detector used may be selected by the person skilled in nucleonic instrument engineering, having regard to the properties of the radiation to be detected, the conditions in which the detector is to be used and the characteristics of radiation which are to be measured. Typically the detectors used are gaseous ionisation detectors, such as Geiger Müller tubes, or scintillation devices including scintillation crystals and organic scintillators. Geiger Müller tubes are preferred detectors for the detector probe of the present invention because of their robustness and wide range of operating temperature. Other forms of detector may be used if suitable although semiconductor detectors are not used in industrial gauges of the type in which the detector probe of the invention is used. This is because they require stable cryogenic cooling in order to reduce noise and are very sensitive to temperature changes. The detector probe may include one or more than one detectors, depending on the intended use of the detector probe. In preferred embodiments of the invention, the detector probe comprises a plurality of detectors, preferably arranged in the form of at least one linear array. When the detector probe is for use in a level gauge or density profiler, it typically has at least 4, preferably at least 10 detectors. Density profilers for use in large vessels may include at least 20 detectors, more preferably at least 40 detectors, spaced apart and preferably arranged as a linear array of detectors. The size of the detectors affects the precision of level detection when the probe is used in a level gauge or density profiler. Therefore the size of detector(s), and their spacing, if more than one detector is used, is selected according to the demands of the use for which the detector probe is designed. When the detector probe is used to find a level (including in a density profile) with high precision then small detectors set in close proximity to each other are preferred. Precision of a level gauge or density profiler can be increased by including overlapping detectors, which may be present in separate detector probes.

The detector probe comprises a support and at least one radiation detector. The at least one radiation detector may be mounted on the support or mounted on an object, such as a circuit board, which is supported by or mounted on the support. By support, we mean any object or structure which can support the detector in the desired position for detecting radiation in use. If sufficiently rigid, a circuit board may itself function as a support. A powered circuit is present to deliver power to the heat source and detector(s), to enable control signals to pass to the detector from a control unit and to carry data signals from the detector to a signal processor and data processor. In a preferred form, the detector is mounted on a printed circuit board for carrying the control and data signals to and from the detector. A printed circuit board may serve as a support for the detector(s). In this form, the circuit board may optionally be provided with a reinforcing structure, such as a stiffening rod or plate in order to provide strength and stiffness over the length of the probe.

The detector probe of the invention is characterised by having an electrically operated source of heat arranged in proximity to one or more of the detectors so that the temperature of the detector(s) may be changed by operation of the heat source. The heat source may be mounted on the support. Typically the heat source may be operated to raise the temperature of more than one of the detectors, for example the temperature of all of the detectors may be raised by the heat source. The heat source may be any device which can be operated to output heat. The heat source may comprise one or more than one point source, i.e. providing heat at a localised area of the probe or it may comprise a distributed source for distributing heat through a greater part of the probe.

When a detector probe is intended for use in a hazardous location, where potentially explosive gas mixtures may be present continuously or intermittently at some time during operation of the probe, the probe and the heat source are designed to be intrinsically safe, as defined by the appropriate standards including the current version of European Standard EN 60079:2009, especially parts 0, 10 and 11 thereof. Intrinsically safe has the meaning given in the standards. Intrinsically safe is a widely used term having a precise meaning that is understood by the skilled person. According to European Standard EN 60079:2009 and British Standard BS EN 60079-11:2012, intrinsic safety is a type of protection based on the restriction of electrical energy within equipment and of interconnecting wiring exposed to the explosive atmosphere to a level below that which can cause ignition by either sparking or heating effects. An intrinsically safe circuit is a circuit in which any spark or any thermal effect produced in the conditions specified in the standard, which include normal operation and specified fault conditions, is not capable of causing ignition of a given explosive atmosphere. An intrinsically safe electrical device is a device in which all of the electrical circuits are intrinsically safe circuits. The design and selection of components and the test criteria applied to such equipment is governed by national and international standards such as BS EN 60079-11:2012 and its related parts, including part 0 concerning general requirements for electrical equipment intended for use in explosive atmospheres. Most preferably, the detector probe conforms to Level of Protection "ia" of the standard, i.e. it is designed to be safe in use in explosive atmospheres when the circuit contains two countable faults as defined in section 5.2 of BS EN 60079-11:2012. Such protection is achieved by the use of various components and construction methods which include, for example, the separation of parts of the circuits by minimum separation distances as set out in section 6.3 "Separation Distances" of BS EN 60079-11:2012.

A preferred source of heat for use in the detector probe is a trace heat source, i.e. a heat source comprising an elongate heating element extending along its length which can be placed into contact with the object which is to be heated. Trace heaters may take the form of a trace heat cable or trace heat tape. Trace heaters may also be known as surface heating elements. Preferably the heat source is a self-regulating heat source i.e. an electrical device incorporating a conducting material having a resistance which is variable according to its temperature. A particularly suitable heat source is a self-regulating heating cable, such as those sold as QTVR cables by Raychem. These cables are designed for maintaining a steady temperature in processes and pipelines. Alternatively other methods of trace heating may be employed using series heaters or constant wattage zone heaters, for example. In a preferred form of the invention the detector probe comprises an elongate support and supported thereon, an electrical circuit board, a plurality of radiation detectors, a heating cable and means to power the heating cable. When the source of heat is not a self-regulating heat source, a temperature sensor and a control system are preferably provided in order to operate the heat source and to prevent over-heating of the probe.

The heat source is preferably operated to maintain the temperature of the probe within a temperature range in which the operation of the detectors, including their associated electronics components, is known or certified to be reproducible and also within a range of temperatures in which the materials of the probe have adequate mechanical strength and resilience to mechanical or thermal shock. Preferably the probe is maintained within a temperature range of 150 to −55° C. (150 to minus 55° C.), more preferably 110 to −55° C. One or more temperature sensors may be provided to monitor the temperature at one or more locations within the probe. The temperature sensor may form part of a feedback system to operate the heat source in response to the temperature detected by the temperature sensor.

The detector probe comprising the detectors, electrical components, such as circuit boards, and heat source, is preferably surrounded by a protective layer, such as a plastic tube. The detector probe comprising the detectors, electrical components and heat source, all optionally surrounded by a protective layer, is preferably housed within a protective housing, preferably formed from a tough and rigid material. The housing is made from a material which is sufficiently transparent to the radiation to be detected by the detectors for the detector probe to perform its function. A suitable material for the housing is titanium which can be formed to be sufficiently strong at a thickness which remains substantially transparent to gamma radiation. In use the detector probe may be placed within a dip tube or dip pipe. The probe preferably further comprises a thermally insulating material arranged between the detectors and the electronic components of the probe and an external housing in order to help maintain the temperature of the detectors at a desired temperature. Normally the insulation must be provided in as thin a layer as possible, in order to reduce the dimensions of the probe. For this reason, insulating materials having a very low thermal conductivity are preferred and the skilled person will appreciate that the selection of a suitable material is dependent upon the characteristics required. In one embodiment, we have found that a suitable thermal insulator has a thermal conductivity($\kappa$)<0.05 W/m/K, and especially <0.005 W/m/K. The insulation may or may not include evacuated compartments. We have found that vacuum insulated panels such as VIP supplied by NanoPore Inc. are suitable. A preferred form of detector probe, suitable for use in a level gauge or density profiler, comprises an elongate support and supported thereon, an electrical circuit board, a plurality of radiation detectors and a heat source, all enclosed within a dip pipe, and thermal insulation between the inner wall of the dip pipe and the detectors. More preferably, the support, carrying the detectors, circuit board and heat source are surrounded by a protective layer, such as a plastic tube, and the thermal insulation is placed between the protective layer and the inner walls of the dip pipe.

The level gauge of the invention comprises a source of ionising radiation and a detector probe as hereinbefore described, said source and detector probe being arranged so that ionising radiation from the source passes along a straight line through a portion of the container to the detector probe. The source is mounted within a shielding material which includes collimation means for producing a collimated beam of radiation which is directed towards the detectors. The source and/or detector probe may be mounted outside or inside a vessel containing the material to be measured. When the source is mounted outside the vessel and the radiation is to traverse at least one vessel wall, the source must be selected to produce radiation of sufficient energy to penetrate the walls of the vessel. The source should also be selected to be of sufficient activity to produce sufficient counts in the detector(s) in order that a reproducible signal may be generated by the detectors which is proportional to the radiation detected within about a second so that level measurement may be carried our reasonably quickly.

The radiation comprises ionising radiation including alpha particles, beta particles, gamma radiation and neutrons. Preferably the ionising radiation detected by the detectors does not include X-rays. The source of ionising radiation is preferably not a source of X-rays. The radiation used is selected by the transparency to the radiation of the vessel and/or its contents (i.e. the attenuation coefficient of the medium) and the availability of suitable sources and detectors. Gamma radiation is preferred because it is useful for scanning large solid structures such as process vessels. Suitable sources of gamma include $^{60}Co$ and $^{137}Cs$, $^{133}Ba$, $^{241}Am$, $^{24}Na$ and $^{182}Ta$, however any gamma-emitting isotope of sufficient penetrating power could be used, and many such are already routinely used in level measurement devices. For a permanent installation, a radioisotope source should be chosen to have a relatively long half-life to give the equipment a satisfactory service life. Usually, the half-life of the radioisotope used will be at least 2, and desirably at least 10, years. The half-lives of the radioisotopes mentioned above are: $^{137}Cs$ gamma ca. 30 years, $^{133}Ba$ ca. 10 years and $^{241}Am$ ca. 430 years. Suitable sources generally emit radiation at energies between about 40 and 1500 keV and suitable detectors can detect such radiation with sufficient sensitivity that the radiation detected varies according to the density of the transmission medium. Desirably the source intensity will be at least about $4 \times 10^7$ more usually from $4 \times 10^8$ to $4 \times 10^9$, Becquerel (Bq). The use of sources with lower intensity may require unduly long integration times to obtain adequately precise results (signal to noise ratio) and more intense sources are relatively expensive and/or may lead to swamping of the detectors. $^{241}Am$ and $^{137}Cs$ sources having an intensity of about $1.7 \times 10^9$ Bq are readily commercially available and are suitable for use in this invention.

One or more than one sources may be used in the level gauge. Normally the number of sources used is not more than 10 and is preferably from 1-4. Each source may emit a beam of radiation towards more than one detector, generally from 4-10 detectors, but from 2-40 detectors may be used, depending on the size/detection area of each detector and the resolution required of the apparatus.

The level gauge is particularly suitable for determining the location in a vessel of a phase boundary between two fluid phases although its application to vessels containing solid phases is not excluded. A widespread application for such apparatus is the determination of a condensed phase (preferably liquid) level in a vessel containing a liquid and a gas phase (which may be e.g. air, a vacuum or a headspace vapour). The phase boundary determined by the method of the invention is then the liquid level. The vessel may alternatively contain more than one liquid phase, e.g. an aqueous and an organic phase, such as oil and water.

A density profiler according to the invention, for measuring a level of two or more material phases within a vessel, comprises a linear array of sources of radiation, at least one detector probe for detecting ionising radiation, each detector probe comprising a linear array of radiation detectors mounted on a support, and a signal and data processing means for calculating a density profile of the material phases using signals generated by the detectors in response to radiation received from the sources; said source array and detector probe being arranged so that ionising radiation from each source passes along a straight line through a portion of the container to a detector carried on the detector probe. The sources are collimated to provide at least one beam of radiation, each beam being directed to one detector located on a detector probe. The relative attenuation of the beams of radiation detected by different detectors, which are located at different positions in the material phases, may be used to calculate a density profile of the material phases.

The source array of a density profiler according to the invention includes a plurality of radiation sources, which are preferably sources of gamma radiation. The energy of the source radiation is typically not more than about 1400 keV and may be lower than this. Preferably the energy of the source radiation is not less than about 30 keV. The source can be a radioactive isotope as described above in connection with the level gauge. When the instrument is intended to be fitted into a vessel such as an oil separator through a standard port, the beam length is preferably less than 50 cm, more preferably less than 30 cm and for this use a less energetic source is thus desirable and energies of less than 500 keV, particularly less than 300 keV and optimally less than 100 keV, are desirable in this invention. Suitable low-energy sources include in particular $^{241}Am$ which is a 60 keV gamma source. For higher energy sources such as $^{137}Cs$, a greater path length is optimal, typically between 20 cm and 40 cm, or more, depending on the particular use for which the density profiler is intended. Other radioisotope sources can be used if desired. The skilled person will select the type, number and size of source which is required. The use of low-energy sources makes equipment handling and source shielding safer and/or easier.

The source shielding and collimation means is shaped so that the emission of radiation is confined, so far as possible, to a beam of suitable width directed through the fluid medium and possibly through vessel walls if required towards one or more detectors. Normally this is achieved by providing a channel or aperture through the shielding material surrounding the source such that emission of radiation from the source is substantially confined to emission of a beam of radiation through the channel. It is often desirable to collimate the source radiation into more than one beam, e.g. by providing more than one channel in the shielding material, so that radiation from a single source may be directed at more than one detector. In this case, the detectors may be in different positions within or outside the vessel and they may form part of the same detector probe or they may be located in different detector probes.

The electronic apparatus of the nucleonic instrument, comprising the control system, signal and data processing device, power source and optionally equipment such as data loggers and transmitting equipment, is normally housed within an enclosure in order to protect it from the environment. The enclosure is designed to withstand the conditions in which nucleonic instrument may be deployed, including those of super-ambient temperature and pressure. The enclosure or housing may comprise a domed cover. The enclosure may be supported mounted adjacent to the detector probe and source array or may alternatively be mounted in a position which is spaced apart from the detector probe. In the latter case, communication means, which may be wireless or wired, are provided to carry electrical signals between the detector probe and the electronic apparatus.

BRIEF DESCRIPTION OF THE DRAWING FIGURES

Figure 2:
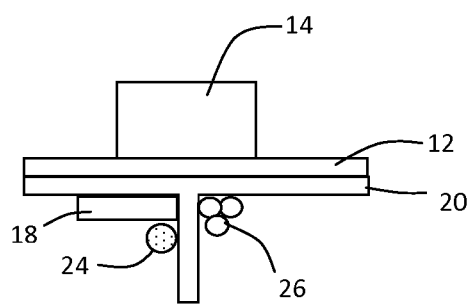
Figure 3:
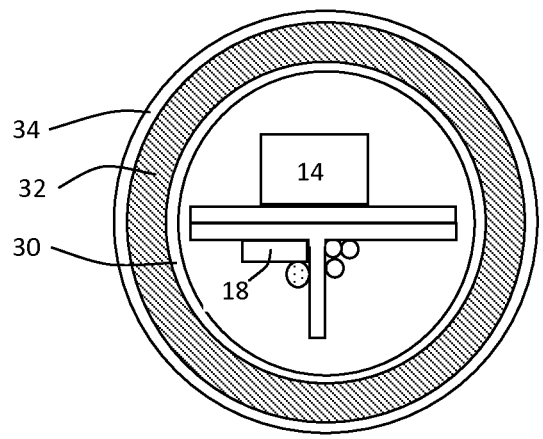
Figure 4:
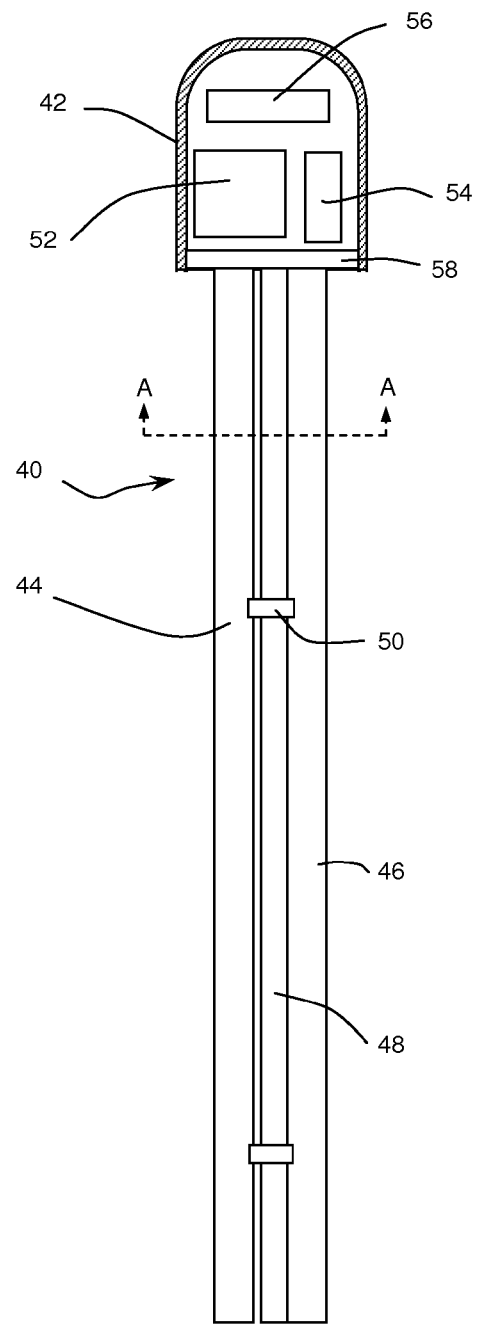
Figure 4A:
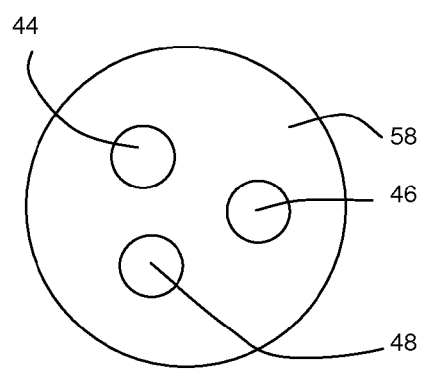

The invention is further described, by way of example only, with reference to the accompanying drawings, which are:

FIG. 1: A schematic diagram of a detector probe according to the invention;

FIG. 2: A schematic diagram of transverse section through a detector probe according to the invention;

FIG. 3: A section through a second embodiment of a detector probe according to the invention;

FIG. 4: A schematic diagram, partially in longitudinal section of a density profiler according to the invention;

FIG. 4A: A schematic diagram of transverse section through line A-A of FIG. 4.

DETAILED DESCRIPTION OF THE INVENTION

FIG. 1 shows a sketch view of a detector probe 10, comprising a support incorporating a printed circuit board 12. A plurality of detectors 14 are mounted on the circuit board in a linear arrangement. A trace heating cable 18 is installed in close proximity to the detectors. A section through a detector probe is shown in FIG. 2. A circuit board 12, carrying Geiger-Müller (GM) tubes 14, is mounted on a support board 20, having a perpendicular portion to form a T-shaped cross-section. Power cables 24, carrying a high voltage supply to the GM tubes, and data cables 26 for carrying signals from the GM tubes to counting modules in a control housing, are run along the angle of the T-shaped support board. The detector probe of FIG. 2 is shown in FIG. 3 installed within a protective tubular enclosure 30 which is then installed within a cylindrical dip pipe 34. Insulation 32 is provided between the tube 30 and the dip pipe.

FIG. 4 shows an elevation of a density profiler instrument 40 according to a preferred embodiment of the invention. The instrument comprises a steel housing 42, shown in section, comprising a support structure 58 and a domed cover 42. The housing contains at least a high voltage generator 52, data loggers, counters, signal processing means and data processors 54, means for supplying power to the voltage generator 56 and electrical equipment and means for transmitting information between the data processors and an external location. The housing also supports a source array housed in tube 44 and two detector probes, housed in tubes 46 and 48. The tubes are braced together for stability by braces 50. FIG. 4A shows a transverse section through the instrument along lines A-A and shows the configuration of the tubes 44, 46, 48 relative to each other and the housing 42.

The invention claimed is:

1. A level gauge or density profiler comprising at least one source of ionising radiation and a detector probe for detecting the ionising radiation, the detector probe comprising:
at least 10 radiation detectors adapted for detecting ionising radiation comprising alpha particles, beta particles, gamma radiation and/or neutrons, the radiation detectors being supported along an elongate support, wherein
an electrically operated self-regulating distributed heat source is arranged along the elongate support in proximity to the detectors so that the temperature of the detectors may be changed by operation of the distributed heat source, the heat source being an electrical device incorporating a conducting material having a resistance which is variable according to a temperature of the heat source, and
the radiation detectors, support and distributed heat source are enclosed within a dip pipe and there is thermal insulation between an inner wall of the dip pipe and the detectors.

2. The level gauge or density profiler according to claim 1, wherein said detectors are selected from the group consisting of Geiger-Müller tubes and scintillation detectors.

3. The level gauge or density profiler according to claim 1, wherein each detector is mounted on a printed circuit board for carrying the control and data signals to and from the detector.

4. The level gauge or density profiler according to claim 3, wherein said support comprises a reinforcing structure for reinforcing the circuit board to provide strength and stiffness over the length of the probe.

5. The level gauge or density profiler according to claim 1, wherein the distributed heat source distributes heat through a greater part of the probe.

6. The level gauge or density profiler according to claim 1, wherein the distributed heat source comprises a trace heat source.

7. The level gauge or density profiler according to claim 1, further comprising a temperature sensor.

8. The level gauge or density profiler according to claim 1, wherein the distributed heat source is operable to maintain the detectors within a temperature range of 150 to −55° C.

9. The level gauge or density profiler according to claim 1, which is intrinsically safe, as defined by European Standard EN 60079:2009.

10. A density profiler according to claim 1 for measuring a level of two or more material phases within a container, the density profiler comprising a linear array of sources of ionising radiation, at least one said detector probe for detecting ionising radiation comprising a linear array of radiation detectors, a power source and a signal and a data processor adapted for calculating a density profile of the material phases using signals generated by the detectors in response to radiation received from the sources; said source array and detector probe(s) being arranged so that ionising radiation from each source passes along a straight line through a portion of the container to a detector carried on the detector probe.

11. The level gauge or density profiler according to claim 1, wherein the distributed heat source comprises a heating cable.

12. The level gauge or density profiler according to claim 1, wherein the detector probe is configured to be maintained in a temperature range of 110° C. to −55° C.

13. The level gauge or density profiler according to claim 1, wherein the detector probe is surrounded by a protective layer comprising a plastic tube.

14. The level gauge or density profiler according to claim 1, wherein the detector probe is housed in a titanium housing.

15. The level gauge or density profiler according to claim 1, wherein the titanium housing has a thickness that renders the titanium housing substantially transparent to gamma radiation.

16. The level gauge or density profiler according to claim 1, wherein the thermal insulation has a thermal conductivity <0.05 W/m/K.

17. The level gauge or density profiler according to claim 1, wherein the heat source is a self-regulating heating cable.

* * * * *